(12) United States Patent
Baird et al.

(10) Patent No.: US 10,123,867 B2
(45) Date of Patent: *Nov. 13, 2018

(54) METHODS AND SYSTEMS FOR MATERIAL FIXATION

(71) Applicant: Cayenne Medical, Inc., Scottsdale, AZ (US)

(72) Inventors: Kevin N. Baird, Phoenix, AZ (US); Derek J. Harper, Scottsdale, AZ (US)

(73) Assignee: Cayenne Medical, Inc., Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/254,870

(22) Filed: Sep. 1, 2016

(65) Prior Publication Data

US 2016/0367356 A1    Dec. 22, 2016

Related U.S. Application Data

(62) Division of application No. 14/055,758, filed on Oct. 16, 2013, now Pat. No. 9,452,042.

(60) Provisional application No. 61/717,569, filed on Oct. 23, 2012.

(51) Int. Cl.
    *A61F 2/08* (2006.01)

(52) U.S. Cl.
    CPC ..... *A61F 2/0811* (2013.01); *A61F 2002/0835* (2013.01); *A61F 2002/0852* (2013.01); *A61F 2002/0882* (2013.01); *A61F 2002/0888* (2013.01); *A61F 2250/0071* (2013.01)

(58) Field of Classification Search
    CPC ............ A61F 2/0811; A61F 2002/0888; A61F 2002/0835; A61F 2002/0852; A61F 2002/0882; A61F 2250/0071; A61F 2002/0817; A61F 2002/0823
    See application file for complete search history.

(56) References Cited

U.S. PATENT DOCUMENTS

| 5,531,792 A | 7/1996 | Huene |
| 5,707,395 A | 1/1998 | Li |
| 6,221,107 B1 | 4/2001 | Steiner |

(Continued)

FOREIGN PATENT DOCUMENTS

| EP | 0834280 A1 | 4/1998 |
| JP | 2009530033 A | 8/2009 |

(Continued)

OTHER PUBLICATIONS

International Search Report and Written Opinion in related PCT Application US2013/065310. International Filing Date Oct. 16, 2013.

(Continued)

*Primary Examiner* — Christopher D Prone
*Assistant Examiner* — Rokhaya Diop
(74) *Attorney, Agent, or Firm* — Schwegman Lundberg & Woessner, P.A.

(57) ABSTRACT

A system and method for making an orthopedic repair by fixing a soft tissue graft to bone, utilizes an implant including a body wedge having first and second outwardly expandable wedge portions, a wing portion having outwardly expandable wings, and a deployment member which is movable distally into the implant to deploy the wedge portions and the wings into an expanded deployed orientation.

18 Claims, 7 Drawing Sheets

(56) References Cited

U.S. PATENT DOCUMENTS

| | | | |
|---|---|---|---|
| 6,482,210 | B1 | 11/2002 | Skiba et al. |
| 6,833,005 | B1 | 12/2004 | Mantas |
| 7,879,094 | B2 | 2/2011 | Baird et al. |
| 8,206,446 | B1 | 6/2012 | Montgomery |
| 2002/0013608 | A1 | 1/2002 | ElAttrache et al. |
| 2006/0155287 | A1 | 7/2006 | Montgomery et al. |
| 2011/0184516 | A1* | 7/2011 | Baird .................... A61F 2/0811 623/13.14 |

FOREIGN PATENT DOCUMENTS

| | | |
|---|---|---|
| JP | 2010507467 A | 3/2010 |
| WO | WO-9639105 A1 | 12/1996 |
| WO | WO-2008073588 A2 | 6/2008 |
| WO | WO-2014066116 A1 | 5/2014 |

OTHER PUBLICATIONS

"U.S. Appl. No. 14/055,758, Final Office Action dated Mar. 10, 2016", 12 pgs.

"U.S. Appl. No. 14/055,758, Non Final Office Action dated Mar. 31, 2015", 14 pgs.

"U.S. Appl. No. 14/055,758, Notice of Allowance dated May 31, 2016", 5 pgs.

"U.S. Appl. No. 14/055,758, Response filed May 10, 2016 to Final Office Action dated Mar. 10, 2016", 7 pgs.

"U.S. Appl. No. 14/055,758, Response filed Sep. 30, 2015 to Non Final Office Action dated Mar. 31, 2015", 8 pgs.

"Australian Application Serial No. 2013335047, First Examination Report dated Jun. 19, 2017", 5 pgs.

"European Application Serial No. 13848294.8, Extended European Search Report dated May 2, 2016", 7 pgs.

"European Application Serial No. 13848294.8, Response filed Sep. 13, 2016 to Extended European Search Report dated May 2, 2016", 18 pgs.

"European Application Serial No. 13848294.8, Response filed Nov. 20, 2015 to Communication pursuant to Rules 161(1) and 162 EPC dated Jun. 3, 2015", 7 pgs.

"International Application No. PCT/US2013/065310, International Preliminary Report on Patentabilty dated May 7, 2015", 9 pgs.

"Japanese Application Serial No. 2015-539661, Office Action dated Oct. 18, 2016", (W/ English Translation), 4 pgs.

"Japanese Application Serial No. 2015-539661, Response filed Jan. 6, 2017 to Office Action dated Oct. 18, 2016", (W/ English Translation of Claims), 8 pgs.

"Australian Application Serial No. 2013335047, Response filed Nov. 28, 2017 to First Examination Report dated Jun. 19, 2017", 22 pgs.

"Australian Application Serial No. 2013335047, Subsequent Examiners Report dated Nov. 28, 2017", 4 pgs.

"Australian Application Serial No. 2013335047, Response filed Jan. 19, 2018 to Subsequent Examiners Report dated Nov. 28, 2017", 16 pgs.

* cited by examiner

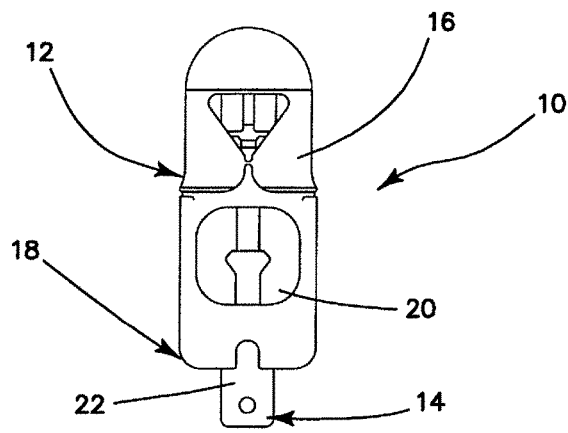
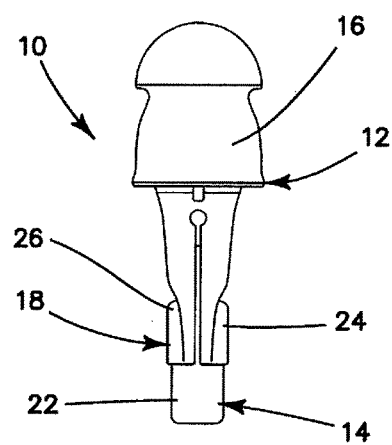
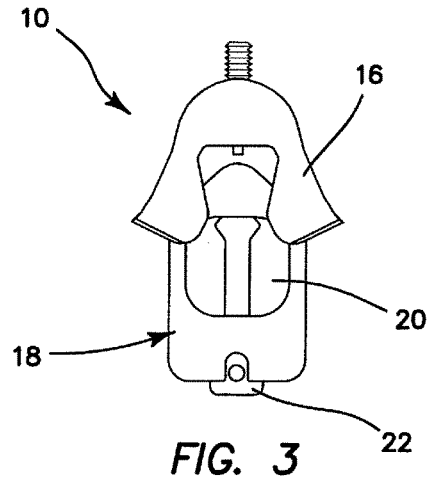
FIG. 1
FIG. 2
FIG. 3

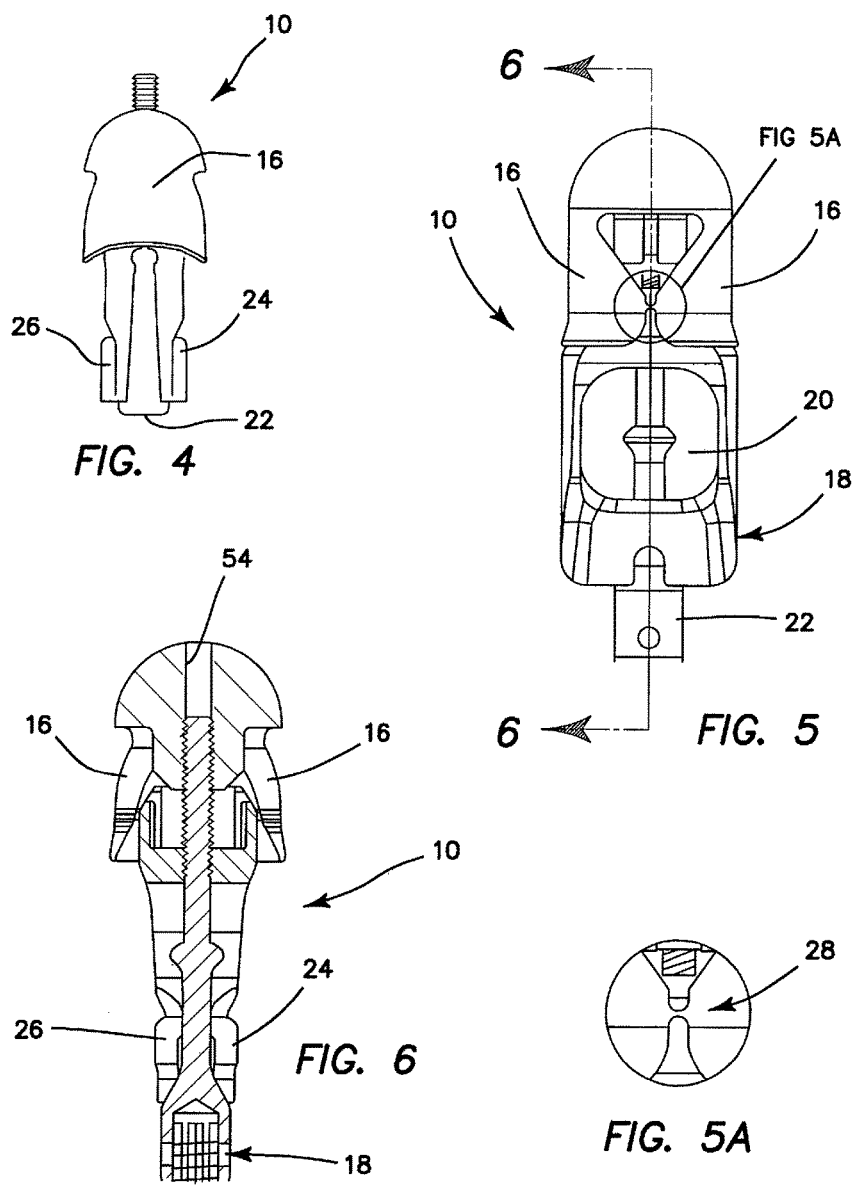

METHODS AND SYSTEMS FOR MATERIAL FIXATION

This application is a divisional under 35 U.S.C. 120 of commonly assigned U.S. application Ser. No. 14/055,758, filed on Oct. 16, 2013 and entitled Methods and Systems for Material Fixation, now allowed, which in turn claims the benefit under 35 U.S.C. 119(e) of the filing date of Provisional U.S. Application Ser. No. 61/717,569, entitled Methods and Systems for Material Fixation, filed on Oct. 23, 2012, which applications are each herein expressly incorporated herein by reference, in their entirety.

This application is also related to commonly assigned U.S. Pat. Nos. 7,879,094 and 8,206,446, both herein also expressly incorporated by reference in their entirety.

BACKGROUND OF THE INVENTION

The present invention relates generally to devices, systems and methods for material fixation. More particularly, the invention relates to a new and novel tendon-to-bone fixation system.

One of the most common needs in orthopedic surgery is the fixation of tendon to bone. The fixation of diseased tendons into a modified position is called tenodesis and is commonly required in patients with injury to the long head of the biceps tendon in the shoulder. In addition, tendons which are torn from their insertion site into bone also frequently require repair. This includes distal biceps tendon tears, rotator cuff tears, and torn flexor tendons in the hand. Tendons are also frequently used in the reconstruction of unstable joints. Common examples include anterior cruciate ligament and collateral ligament reconstructions of the knee, medial and lateral elbow collateral ligament reconstructions, ankle collateral ligament reconstruction, finger and hand collateral ligament reconstructions and the like. The commonly assigned U.S. Pat. Nos. 7,879,094 and 8,206,446, already incorporated by reference herein, describe devices and techniques for performing these types of procedures, utilizing, for example, the AperFix® femoral implant.

Currently, two different sources are utilized for the tissue that replaces the injured native Anterior Cruciate Ligament (ACL). When the new tissue comes from the patient's own body, the new graft is referred to as an "autograft", and when cadaveric tissue is used, the new graft is referred to as an "allograft". The most common autograft ACL reconstruction performed currently is the bone-patellar tendon-bone (BTB) graft. The BTB graft fixed with an interference screw is used more often because it more accurately replicates the native ACL due to its aperture compression at the femoral tunnel aperture. However, BTB reconstructions result in an increased rate of anterior knee pain post-surgically for periods of up to three years after reconstruction. Additionally, the harvest procedure for the BTB autograft is invasive, and can be difficult to perform. Alternatively, the hamstring tendon autograft ACL reconstruction technique does not result in any significant post-surgical pain, and the harvest procedure is minimally invasive compared to the BTB graft harvest. The reason that the hamstring tendon autograft procedure is not used more frequently in ACL reconstructions is that the fixation of the hamstring tendons to the femur and tibia are not as strong as the fixation of the BTB autografts.

Many systems have addressed some of the problems associated with ACL reconstruction using hamstring tendons, but there is not one system that addresses them all. The EndoButton by Smith & Nephew is easy to use and does not need additional drill holes. However, it does require additional accessories and additional people to perform the procedure, and does not replicate the native ACL due to a lack of tendon-to-bone compression at the aperture as well as additional length of tendon between fixation points. The EndoButton is an example of a cortical-only hamstring fixation device that yields a longer graft construct, resulting in a graft that is less stiff than the native ACL. Peer-reviewed journal data show that existing soft tissue fixation systems with long graft lengths between fixation points have as much as a 56% reduction in graft stiffness when compared to the native ACL.

The Arthrex TightRope DB is also a cortical fixation device that also incorporates a wedge that is pulled between the tendon bundles. This separates the bundles, but the wedge doesn't expand.

The Rigid Fix by Mitek is a cross-pin device that requires multiple drill holes, additional instruments, and assistance from other people in the operating room to complete the repair. Also, there is only passive compression of tendon-to-bone, not direct, active compression.

The Stratis ST by Scandius attempts to more accurately replicate the native ACL by adding material to take up space in the femoral tunnel, resulting in more intimate contact between the tendon and the bone. However, to insert the device into the femoral tunnel, the cross-sectional area must be less than the cross-sectional area of the hole. Therefore, there is no real compression of tendon to bone. The Stratis ST also requires additional drill holes, accessories, and people to perform the procedure.

EZLoc, by Arthrotek gives high strength and attempts to more accurately replicate the native ACL in the same fashion as the Stratis ST by taking up the space in the tunnel. This does create more intimate contact between the tendon and bone, but does not offer real compression at the aperture.

The Mitek Femoral IntraFix is an interference screw device that incorporates a sheath to protect the graft during screw insertion. Since it is a compression device, there is no active engagement of the implant with the tunnel wall.

Interference screws such as the RCI screw by Smith & Nephew and RetroScrew by Arthrex are easy to use and provide compression of tendon to bone at the femoral tunnel aperture. However, the pull-out strength and stiffness of the repair are significantly lower than in the preceding systems.

SUMMARY OF THE INVENTION

The invention seeks to improve the tendon-bone fixation of hamstring autografts as well as other soft tissue ACL reconstruction techniques. The device is easy to use, provides high fixation of tendon-bone and active tendon-bone compression, requires no additional accessories, uses only one drill hole, and can be implanted by one person. The device replicates the native ACL by compressing the tendons against the bone at the aperture of the femoral tunnel, effectively shortening the length of the graft, which leads to a shorter graft and increased graft stiffness as compared to cortical-only hamstring fixation devices. It also provides strength greater than 1,000 N (Newtons), which is desirable for ACL reconstruction systems.

The device of the present invention is indented for use in tenodesis procedures with soft tissue grafts, utilizing either arthroscopic or open techniques during ACL, Posterior Cruciate Ligament (PCL), Medial Collateral Ligament (MCL), Lateral Collateral Ligament (LCL), and Medial Patellofemoral Ligament (MPFL) reconstruction. During a ligament reconstruction procedure, soft tissue grafts are attached to the femur utilizing the device. Soft tissue grafts are typically harvested from the patient's ipsilateral leg, but cadaveric tissue is also acceptable. The device also provides active compression of the tendons at the aperture of the bone tunnel.

Minimizing the removal of bone and providing a device that is able to be used in tunnels under 25 mm are important in tenodesis procedures. The device of the present invention is a shorter version of the AperFix® Femoral implant, commercially available from the assignee and disclosed in prior U.S. Pat. No. 7,879,094.

More particularly, there is provided an implant for affixing soft tissue to bone, which comprises a body wedge having first and second outwardly expandable wedge portions, a wing portion having outwardly expandable wings, which is connected to a distal end of the body wedge, and a deployment member which is movable distally into the implant to deploy the wedge portions and the wings into an expanded deployed orientation. When the wings are in their expanded deployed orientation, portions of the wings extend proximally over distal portions of the body wedge. Advantageously, a breakaway connection is provided between two of the outwardly expandable wings to hold them together in an undeployed retracted orientation, until the deployment member advances distally a sufficient distance to break the connection deploy the wings outwardly. The breakaway connection, in the disclosed embodiments, comprises a wing breakaway tab.

The deployment member comprises a screw, which comprises an enlarged head for deploying the wedge portions outwardly when the head advances distally to a position between the wedge portions. The screw further comprises a threaded shank distal to the head. A tendon eyelet is provided in the wedge body for receiving soft tissue therein.

Outer keys are provided on the wing portion, and corresponding keyways are provided on the outer wedge body which are adapted to engage with one another to prevent the wings from rotating relative to the body wedge during implant deployment. Additionally, a wing deployment surface on the wing portion and a corresponding body wedge deployment surface on the body wedge are arranged so that, during deployment of the wings and body wedge portions, the wing deployment surface and the body wedge deployment surface slidably engage one another to cause the wings to bend around wing flex radii and thereby urge a bone engagement edge on the wing portion to start engaging radially into the bone.

In another aspect of the invention, there is provided an implant for affixing soft tissue to bone, which comprises a body wedge having first and second outwardly expandable wedge portions, a wing portion having outwardly expandable wings, which is connected to a distal end of the body wedge, and a deployment member which is movable distally into the implant to deploy the wedge portions and the wings into an expanded deployed orientation. Advantageously, a breakaway connection is provided between two of the outwardly expandable wings to hold them together in an undeployed retracted orientation until the deployment member advances distally a sufficient distance to break the connection deploy the wings outwardly. The breakaway connection, in the disclosed embodiments, comprises a wing breakaway tab.

The deployment member comprises a screw, which comprises an enlarged head for deploying the wedge portions outwardly when the head advances distally to a position between the wedge portions. The screw further comprises a threaded shank distal to the head. A tendon eyelet is provided in the wedge body for receiving soft tissue therein.

Outer keys are provided on the wing portion, and corresponding keyways are provided on the outer wedge body which are adapted to engage with one another to prevent the wings from rotating relative to the body wedge during implant deployment. Additionally, a wing deployment surface on the wing portion and a corresponding body wedge deployment surface on the body wedge are arranged so that, during deployment of the wings and body wedge portions, the wing deployment surface and the body wedge deployment surface slidably engage one another to cause the wings to bend around wing flex radii and thereby urge a bone engagement edge on the wing portion to start engaging radially into the bone.

In still another aspect of the invention, there is disclosed a method of making an orthopedic repair by fixing a soft tissue graft to bone, which comprises a step of placing a soft tissue graft on an implant. The implant comprises a body wedge having first and second outwardly expandable wedge portions, a wing portion having outwardly expandable wings which is connected to a distal end of the body wedge, and a deployment member which is movable distally into the implant to deploy the wedge portions and the wings into an expanded deployed orientation. The method further comprises steps of disposing the implant within a bone tunnel at a desired location, such that a plurality of ends of the soft tissue graft extend from the implant in a proximal direction through the bone tunnel, deploying the wedge portions of the implant outwardly to engage portions of the plurality of ends of the soft tissue graft and push the soft tissue graft ends into contact with adjacent bone, and deploying the wing portions outwardly so that wing portions engage adjacent bone to fix the implant in place within the bone tunnel, wherein the wing portions deploy proximally over portions of the body wedge.

The deploying steps are performed by advancing a lead screw distally into the implant, in a disclosed embodiment.

The wing portions deploying step is performed by advancing a deployment member distally into the implant and breaking a breakaway tab connecting the wing portions together in their undeployed orientation. The breakaway tab ensures that the wings do not deploy or partially deploy prematurely.

The invention, together with additional features and advantages thereof, may best be understood by reference to the following description taken in conjunction with the accompanying illustrative drawing.

BRIEF DESCRIPTION OF THE DRAWINGS

FIG. 1 is an elevational view of an embodiment of an implant constructed in accordance with the principles of the present invention, in an undeployed state;

FIG. 2 is a rotated view of the implant of FIG. 1;

FIG. 3 is a view similar to FIG. 1, with the implant in a deployed state;

FIG. 4 is a rotated view of the implant of FIG. 3;

FIG. 5 is an elevational view of the implant of FIG. 1, in an undeployed state and showing greater detail;

FIG. 5A is an enlarged view of the portion of FIG. 5 denoted by the identified circle;

FIG. 6 is a cross-sectional view of FIG. 5, taken along lines 6-6;

DETAILED DESCRIPTION OF THE INVENTION

Figure 7:
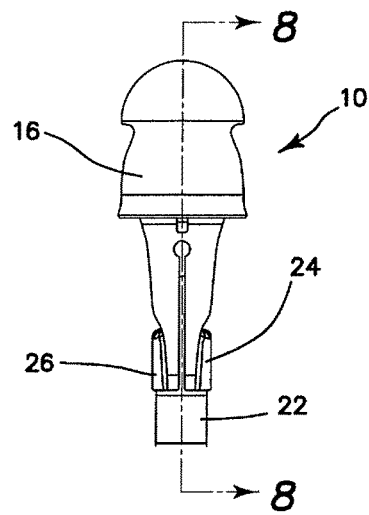
FIG. 7 is an elevational view similar to FIG. 5, with the implant in a rotated orientation.

Referring now more particularly to the drawings, an implant 10 constructed in accordance with the principles of the present invention, having a body 12 comprising three separate major components. These components comprise a quad lead screw 14, wings 16, and a body wedge 18. Tendon eyelets 20 are provided for the loading of tendons thereinto prior to insertion of the implant 10 into a bone tunnel. When the implant 10 is placed into a bone tunnel, the screw 14 is rotated clockwise until a head 22 of the screw 14 slides between portions 24, 26 of the body wedge 18. This expands the base of the implant by forcing the wedge portions 24, 26 outwardly, thereby acting to compress the tendon against the bone tunnel walls. As the screw 14 continues to rotate, the wings 16 slide apart over the body wedge 18 and engage with the walls of the bone tunnel to anchor the implant 10 in place within the tunnel. The engagement of the wings 16 into the bone is what gives the implant the majority of its pullout strength. FIGS. 1 and 2 illustrate the implant 10 in its undeployed state, while FIGS. 3 and 4 illustrate the implant in its deployed state.

Figure 8:
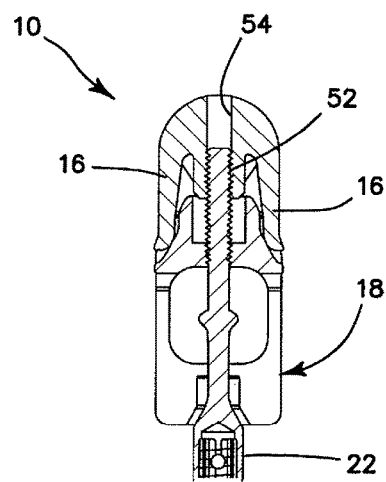
FIG. 8 is a cross-sectional view of FIG. 7, taken along lines 8-8.
Figure 9:
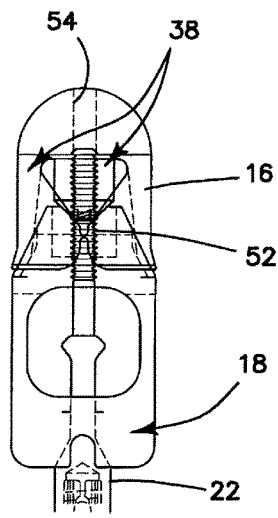
FIG. 9 is an elevational view of the implant of FIG. 5, showing hidden elements in phantom lines.
Figure 10:
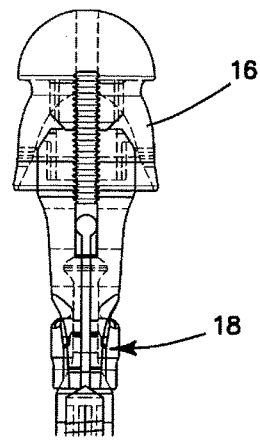
FIG. 10 is an elevational view similar to FIG. 9, wherein the implant is rotated approximately one-quarter turn.
Figure 11:
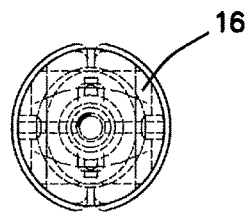
FIG. 11 is a top view of the implant of FIG. 9.
Figure 12:
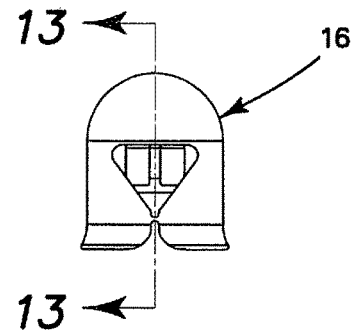
FIG. 12 is an elevational view of the wings portion of the implant of the present invention, shown in an undeployed state and in isolation.
Figure 13:
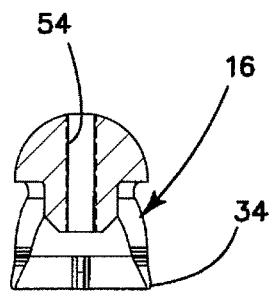
FIG. 13 is a cross-sectional view of FIG. 12, taken along lines 13-13.
Figure 14:
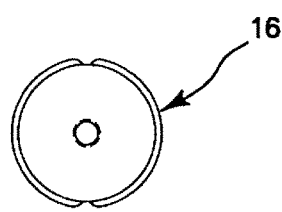
FIG. 14 is a top view of the wings shown in FIG. 12.
Figure 15:
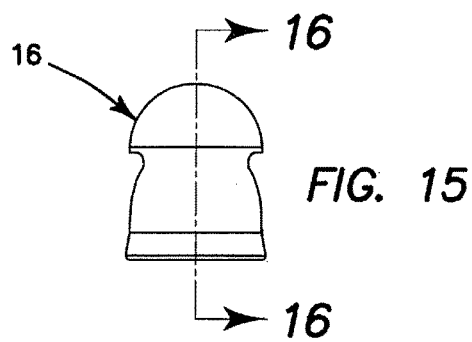
FIG. 15 is an elevational view similar to FIG. 12, with the wings being rotated about one-quarter turn.
Figure 16:
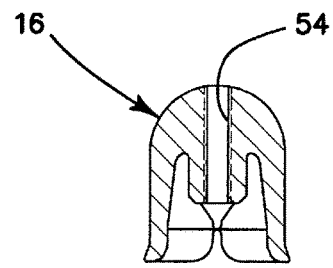
FIG. 16 is a cross-sectional view of the implant of FIG. 15, taken along lines 16-16.
Figures 17, 17A:
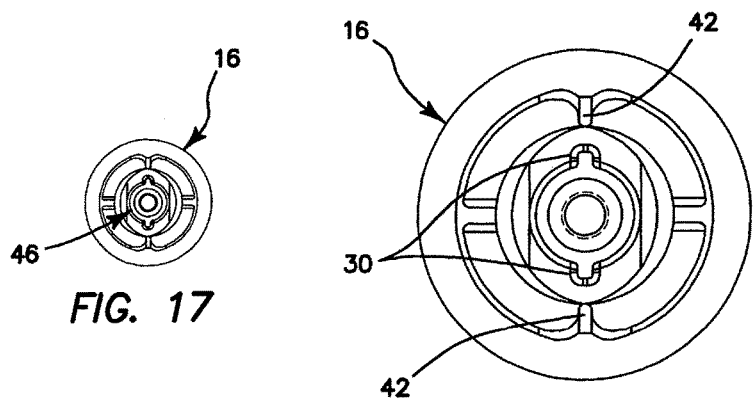
FIG. 17 is a bottom view of the wings of FIG. 12.
FIG. 17A is an enlarged view of FIG. 17.
Figures 18, 19, 20, 21:
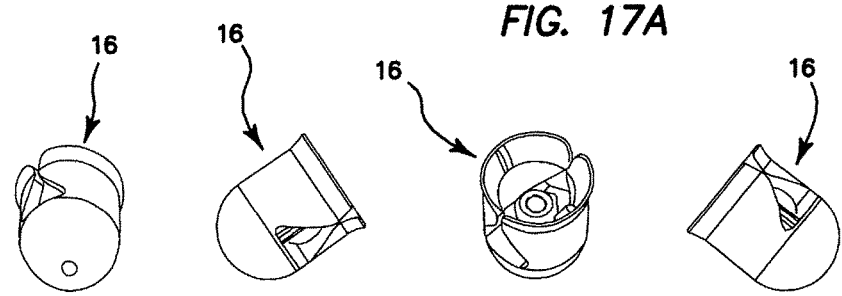
FIGS. 18-25 are isometric views, in varying orientations, of; the wings portion of the present invention.
Figures 22, 23, 24, 25:
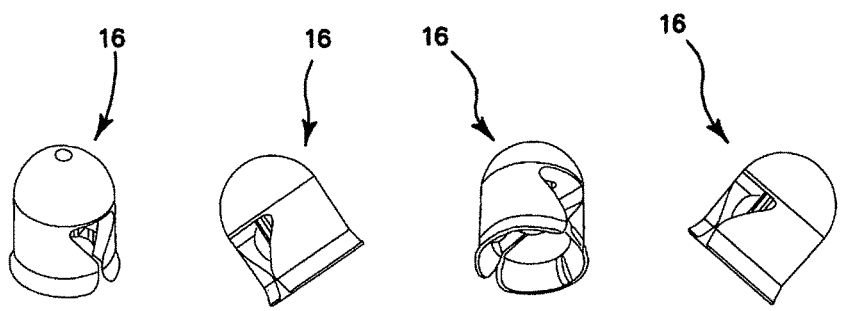

FIGS. 5 and 7 illustrate the inventive implant 10 in its undeployed state, with FIG. 7 being rotated about 90 degrees relative to FIG. 5. FIGS. 6 and 8 are cross-sectional views taken along lines 6-6 of FIG. 5 and 8-8 of FIG. 7, respectively. FIGS. 9 and 10 are rotated views of the implant 10, showing internal components in phantom, while FIG. 11 is a top view of the implant shown in FIG. 9.

Figure 26:
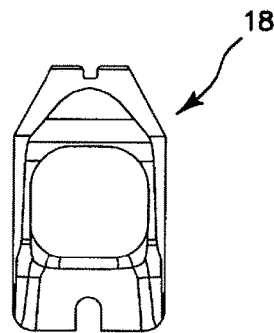
FIG. 26 is an elevational view, in isolation, of the body wedge portion of the inventive implant.
Figure 27:
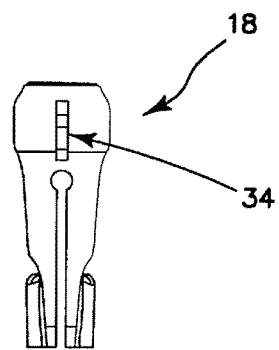
FIG. 27 is an elevational view of the body wedge of FIG. 26 rotated about one-quarter turn.
Figure 28:
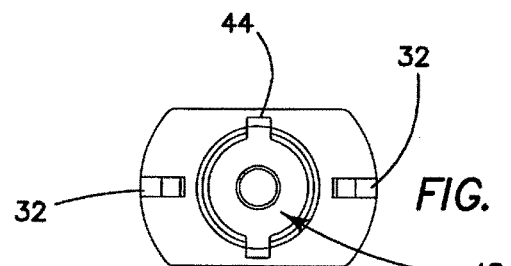
FIG. 28 is a top view of the body wedge of FIG. 26.
Figure 37:
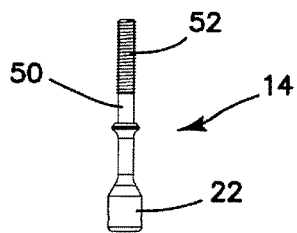
FIGS. 37-40 are isometric views, in varying orientations, of the quad-lead screw portion of the present invention.
Figure 39:
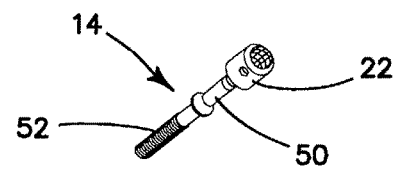
Figure 38:
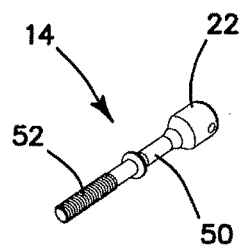
Figure 40:
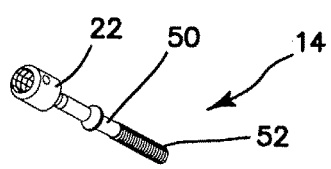
Figure 29:
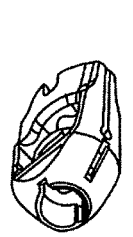
FIGS. 29-36 are isometric views, in varying orientations, of the body wedge portion of the present invention.
Figure 30:
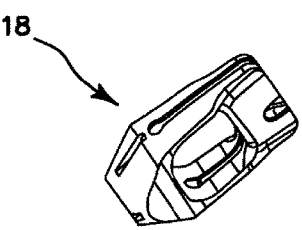
Figure 31:
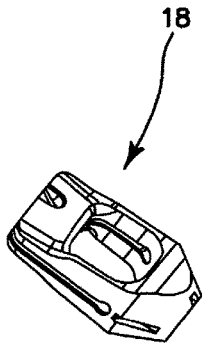
Figure 32:
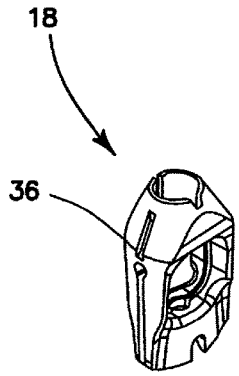
Figure 33:
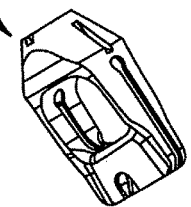
Figure 34:
Figure 35:
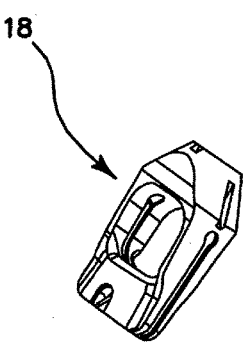
Figure 36:

FIGS. 12-17A are several views, in cross-section, of the wings 16 of the inventive implant 10, while FIGS. 18-25 illustrate the wings 16 from a variety of orientations. FIGS. 26-28 are views of the body wedge 18 from two sides and the top, while FIGS. 29-36 are perspective views, from various orientations, of the body wedge 18. FIGS. 37-40 are isolation views, from various orientations, of the quad lead screw 14.

There are several key features that enable the implant 10 to deploy successfully into bone. A wing breakaway tab 28 (FIG. 5A) is a small web of material that connects both wings 16 together. This prevents the wings 16 from prematurely deploying or partially deploying into the bone tunnel if the implant 10 is inserted and removed from the tunnel during the procedure. The tab 28 breaks and the wings 16 separate once the screw 14 advances completely into the base of the body wedge 18. At this point, the wings 16 may rotate about the body wedge 18, which does not allow the wings 16 to deploy into surrounding bone. However, outer wing keys 30 (FIG. 17A) are engaged with outer body wedge keyways 32 (FIG. 28), which prevent the wings 16 from rotating relative to the body wedge 18. As the screw 14 continues to rotate clockwise, a wing deployment surface 34 (FIGS. 13, 27) slides along a body wedge deployment surface 36 (FIG. 32), and the wings 16 bend around wing flex radii 38 (FIG. 9), urging a bone engagement edge 40 (FIG. 22) to start engaging radially into the bone. Without the bone engagement edge 40, created by a slight flare of the wings 16, the wings would not deploy into harder bone.

As the screw 14 continues to rotate counterclockwise, the outer wing keys 30 slide out of the outer body wedge keyways 32 and inner wing keys 42 (FIG. 17A) engage with inner body wedge keyways 44 (FIG. 28). This continues to prevent the wings 16 from rotating around the body wedge 18, and prevents incomplete deployment. As the screw 14 completes its final clockwise rotation, a wing thread boss 46 (FIG. 17) is pulled into a body wedge counterbore 48 (FIG. 28). The wing thread boss 46 allows the wings 16 to be as short as possible by providing enough thread internal to the wings to prevent stripping in hard bone.

FIGS. 37-40 illustrate the quad lead screw 14 from various angles, which comprises the head 22 and a shank 50 having threads 52. The body 12 of the implant 10 comprises a channel 54 for receiving the threaded shank 50 of the screw 14 as it is advanced into the implant 10, as described above.

Advantageously, in certain applications, the implant 10 of the present invention, which has a length of 24 mm rather than the 29 mm length of the present AperFix femoral implant offered by the assignee, is insertable through the anteromedial portal, which creates a shorter tunnel than the transtibial approach. As noted above, the implant 10 comprises three major components, namely, a body wedge 18, one-piece wings 16, and a central screw 14. The prior AperFix implant comprises a body, a central screw, left and right arms, attached to the body with pins, and a distal wedge for actuating the wings outwardly. By eliminating the two arms and the wedge components of the prior AperFix implant, replacing it with a one-piece wings component, the substantially shorter length is achievable, and the pins for securing the arms are also eliminated.

The present invention, as noted above, includes a breakaway tab to keep the wings together prior to deployment. Without the tab, the wings would prematurely engage the bone. The keys and keyways are an anti-rotation feature to prevent the wings from rotating during initial deployment. Without these features, the wings would not fully deploy. The wedge is now build into the body, causing the wings to flare open into the bone.

Accordingly, although exemplary embodiments of the invention has been shown and described, it is to be understood that all the terms used herein are descriptive rather than limiting, and that many changes, modifications, and substitutions may be made by one having ordinary skill in the art without departing from the spirit and scope of the invention.

What is claimed is:

1. An implant for affixing soft tissue to bone, comprising:
a body wedge comprising first and second outwardly expandable wedge portions;
a wing portion having outwardly expandable wings which is connected to a distal end of the body wedge;
a deployment member comprising a fastener, the fastener being movable distally into the implant and between the wedge portions to deploy the wedge portions outwardly and the wings into an expanded deployed orientation; and
a breakaway connection between two of the outwardly expandable wings to hold them together in an undeployed retracted orientation until the deployment member advances distally a predetermined distance adapted to break the connection and deploy the wings outwardly;
wherein when the wings are in their expanded deployed orientation, portions of the wings extend proximally over distal portions of the body wedge and at least partially cover an outer surface of the body wedge.

2. The implant as recited in claim 1, wherein said breakaway connection comprises a wing breakaway tab.

3. The implant as recited in claim 1, wherein said fastener comprises a screw.

4. The implant as recited in claim 3, wherein said screw comprises an enlarged head for deploying the wedge portions outwardly when the head advances distally to a position between the wedge portions.

5. The implant as recited in claim 4, wherein the screw further comprises a threaded shank distal to the head.

6. The implant as recited in claim 1, and further comprising a tendon eyelet in said wedge body for receiving soft tissue therein.

7. The implant as recited in claim 1, and further comprising outer keys on the wing portion and corresponding keyways on the outer wedge body which are adapted to engage with one another to prevent the wings from rotating relative to the body wedge during implant deployment.

8. The implant as recited in claim 1, and further comprising a wing deployment surface on the wing portion and a corresponding body wedge deployment surface on the body wedge, wherein during deployment of the wings and body wedge portions, the wing deployment surface and the body wedge deployment surface slidably engage one another to cause the wings to bend around wing flex radii and thereby urge a bone engagement edge on the wing portion to start engaging radially into the bone.

9. An implant for affixing soft tissue to bone, comprising:
a body wedge comprising first and second outwardly expandable wedge portions;
a wing portion having outwardly expandable wings which is connected to a distal end of the body wedge;
a deployment member comprising a fastener, the fastener being movable distally into the implant and between the wedge portions to deploy the wedge portions outwardly and the wings into an expanded deployed orientation; and
a breakaway connection between two of said outwardly expandable wings to hold them together in an undeployed retracted orientation until the deployment member advances distally a predetermined distance adapted to break the connection and deploy the wings outwardly, the predetermined distance corresponding to the distance necessary for the fastener to advance entirely within a base of the body wedge.

10. The implant as recited in claim 9, wherein said breakaway connection comprises a wing breakaway tab.

11. The implant as recited in claim 9, wherein said fastener comprises a screw.

12. The implant as recited in claim 11, wherein said screw comprises an enlarged head for deploying the wedge portions outwardly when the head advances distally to a position between the wedge portions.

13. The implant as recited in claim 12, wherein the screw further comprises a threaded shank distal to the head.

14. The implant as recited in claim 9, and further comprising a tendon eyelet in said wedge body for receiving soft tissue therein.

15. The implant as recited in claim 9, and further comprising outer keys on the wing portion and corresponding keyways on the outer wedge body which are adapted to engage with one another to prevent the wings from rotating relative to the body wedge during implant deployment.

16. The implant as recited in claim 9, and further comprising a wing deployment surface on the wing portion and a corresponding body wedge deployment surface on the body wedge, wherein during deployment of the wings and body wedge portions, the wing deployment surface and the body wedge deployment surface slidably engage one another to cause the wings to bend around wing flex radii and thereby urge a bone engagement edge on the wing portion to start engaging radially into the bone.

17. An implant for affixing soft tissue to bone, comprising:
a body wedge comprising first and second outwardly expandable wedge portions;
a wing member having outwardly expandable wings, the wing member connected to a distal end of the body wedge;
a deployment member comprising a fastener, the fastener being movable distally into the implant and between the wedge portions to deploy the wedge portions outwardly and the wings into an expanded deployed orientation, wherein the wing member includes an internally threaded channel adapted to receive a distal end of an externally threaded shaft of the fastener; and
a breakaway connection between two of the outwardly expandable wings to hold them together in an undeployed retracted orientation until the deployment member advances distally a predetermined distance adapted to break the connection and deploy the wings outwardly.

18. The implant as recited in claim 17, wherein the wing member includes a wing deployment surface and the body wedge includes a wedge deployment surface adapted to contact the wing deployment surface when the deployment member is moved distally into the implant.

* * * * *